(12) United States Patent
Hahnen (10) Patent No.: US 6,679,871 B2
(45) Date of Patent: *Jan. 20, 2004

(54) INFLATABLE CANNULA AND METHOD OF USING SAME

(75) Inventor: Kevin Hahnen, Westlake Village, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/751,445

(22) Filed: Dec. 29, 2000

(65) Prior Publication Data

US 2001/0023332 A1 Sep. 20, 2001

Related U.S. Application Data

(63) Continuation-in-part of application No. 09/130,585, filed on Aug. 7, 1998, now Pat. No. 6,168,586.

(51) Int. Cl.[7] .............................................. A61M 31/00
(52) U.S. Cl. .................... 604/509; 604/96.01; 604/506
(58) Field of Search .......................... 604/96–103, 118, 604/500, 502, 507, 508, 509, 96.01, 97.01, 101.01, 101.03, 101.04, 101.05, 102.01, 102.02, 102.03, 103.03, 103.07, 104; 606/191–194

(56) References Cited

U.S. PATENT DOCUMENTS

| | | | | |
|---|---|---|---|---|
| 4,636,195 A | * | 1/1987 | Wolinsky | 604/53 |
| 4,921,483 A | * | 5/1990 | Wijay et al. | 604/96 |
| 5,250,025 A | * | 10/1993 | Sosnowski et al. | 604/51 |
| 5,328,471 A | * | 7/1994 | Slepian | 604/101 |
| 5,419,763 A | | 5/1995 | Hildebrand | |
| 5,558,644 A | * | 9/1996 | Boyd et al. | 604/96 |
| 5,588,961 A | | 12/1996 | Leone et al. | |
| 5,766,151 A | * | 6/1998 | Valley et al. | 604/96 |
| 5,775,327 A | | 7/1998 | Randolph et al. | |
| 5,908,407 A | | 6/1999 | Frazee et al. | |
| 5,928,192 A | | 7/1999 | Maahs | |
| 6,143,015 A | * | 11/2000 | Nobles | 606/194 |
| 6,168,586 B1 | * | 1/2001 | Hahnen | 604/509 |

* cited by examiner

*Primary Examiner*—Brian L. Casler
*Assistant Examiner*—Jennifer Maynard
(74) *Attorney, Agent, or Firm*—O'Melveny & Myers LLP; John Christopher James (57) ABSTRACT

An expandable lumen cannula which includes an elongate tube having a proximal end, a distal end, an intermediate flexible region, and a lumen therebetween. The cannula further includes a balloon occluder mounted on the distal end of the tube. The intermediate flexible region of the tube further includes an elongate generally cylindrical balloon disposed circumferentially about the flexible region which, upon inflation, expands the luminal diameter of the intermediate region. First and second inflation ports are in fluid communication with the balloon occluder and the cylindrical balloon. The cannula may optionally include a cardioplegia port disposed within the distal region of the tube, proximal the balloon occluder and distal the generally cylindrical balloon. Methods of using such a cannula are also disclosed, particularly to provide cannulation through a minimally invasive port incision, and to thereafter displace the tissues and organs adjacent an intercostal access port upon inflation and expansion of the generally cylindrical balloon.

13 Claims, 7 Drawing Sheets

INFLATABLE CANNULA AND METHOD OF USING SAME

This is a continuation-in-part of U.S. application Ser. No. 09/130,585, filed on Aug. 7, 1998, now U.S. Pat. No. 6,168,586, the entirety of which is incorporated herein by reference.

FIELD OF THE INVENTION

This invention relates generally to a cannula or catheter that can be introduced to a small port and be inflated to accommodate a large flow of fluids, or can serve as a conduit or port to apply other medical therapy, such as surgical instruments, dilatation catheters, atherectomy devices, filters, aspirators, and pressure monitors.

BACKGROUND OF THE INVENTION

Minimally invasive surgical procedures which use an endoscopic approach have been widely used in many surgical specialties, including cardiothoracic surgery. New surgical techniques and instruments have been developed especially to assist in minimally invasive coronary bypass grafting. This procedure is often performed using the port access approach where a minimal access incision is made in the intercostal space rather than the traditional midstemotomy approach, therefore minimizing trauma to the chest wall. After the incision is made, various instruments can be inserted through the incision and various tissue layers to reach the heart and great vessels. This peripherally-based system achieves aortic occlusion, cardioplegia delivery, and left ventricular decompression; thus, coronary revascularization and various cardiac procedures can be effectively performed.

Traditionally, flexible catheters or cannulas are fixed in their lumen and outside diameter size. In order to provide a large lumen for oxygenated blood flow during cardiopulmonary bypass (CPB), a traditional catheter or cannula is required to have a large diameter, therefore making insertion and tissue penetration difficult through a small port. A rigid trocar provides adequate luminal dimension; however, it is also limited in its ability to expand and provide easy access. Therefore, a need exists for a fluid or medical instrument delivery catheter or cannula having a flexible and expandable wall and a capability of achieving a minimal profile for entry through a small port, and having an ability to thereafter expand to accommodate a larger luminal diameter for delivery of fluid and instruments.

SUMMARY OF THE INVENTION

The present invention is particularly useful in minimally invasive coronary artery bypass grafting (CABG) since this procedure is generally performed through a small incision. In one embodiment, the invention provides a cannula comprising an elongate tubular member having a proximal end, a distal end, an expandable region, and a lumen. An elongated tubular or cylindrical balloon is disposed circumferentially about the expandable region of the tube. The cylindrical balloon has an inflation port and upon inflation itself expands and also causes the expandable region of the cannula to expand, thus enlarging the luminal diameter of the expandable region. The elongated cylindrical balloon is sealed at its ends to the outer wall of the cannula forming an inflatable space between the outer wall of the expandable region of the cannula and the inner wall of the cylindrical balloon.

In another embodiment, the invention provides an expandable lumen cannula comprising an elongate tubular member having an outer wall, a proximal end, a distal end, and a lumen therebetween. The elongate tubular member is expandable from a compressed condition to an expanded condition, and an elongate balloon having a proximal opening and a distal opening is circumferentially disposed about the elongate tubular member. A plurality of connections connect the outer wall of the elongate tubular member to the inner wall of the elongate balloon. Alternatively, the elongate balloon can be toroidal, forming a lumen from its proximal opening to its distal opening. In this embodiment, the outer wall of the elongate tubular member can be connected to the lumen of the elongate balloon through 1) a series of random connections, 2) a predetermined pattern of connections, or 3) in one continuous seal formed between the outer wall of the elongate tubular member and the lumen of the elongate balloon.

In another embodiment, a balloon occluder is mounted at the distal end of the cannula. Each of the balloon occluder and the cylindrical balloon has its own inflation port. In another embodiment, the cannula has an additional lumen extending distally from the proximal end to a port proximal to the balloon occluder for delivering cardioplegic solution. In other embodiments, the cannula will further include one or more helical threads disposed about the distal end of the tube proximal to the balloon occluder and distal to the cylindrical balloon.

In yet another embodiment, the present invention provides an expandable lumen cannula comprising a first elongate tubular member having a proximal end, a distal end, and a lumen therebetween, and a second elongate tubular member having an outer wall, a proximal end, a distal end, and a lumen therebetween. The second elongate tubular member is expandable and flexible. The proximal end of the second elongate tubular member is connected to the distal end of the first elongate tubular member, and their lumens are in fluid communication with each other. An elongate tubular or cylindrical balloon is disposed circumferentially about the second elongate tubular member, and a plurality of connections are formed between the outer wall of the second elongate tubular member and the elongate balloon.

The elongate balloon can be formed so that it has openings on its proximal and distal ends, which are sealed in a fluid-tight manner to the proximal and distal ends of the second elongate tubular member. A space can thus be formed between the outer wall of the second elongate tubular member and the inner wall of the elongate balloon. The connections can be between the outer wall of the second elongate tubular member and the inner wall of the elongate balloon. An inflation port in communication with the space formed between the second elongate tubular member and the elongate balloon can be used to inflate the elongate balloon with fluid. The fluid will be trapped in the space between the outer wall of the elongate tubular balloon and the inner wall of the elongate balloon and will cause an outward force, thus forcing the elongate balloon to expand and inflate. The inflation of the elongate balloon will in turn cause an outward force on the connections between the elongate balloon and the second elongate tubular member. This force will cause those connections to pull the wall of the second elongate tubular member radially outward, thus increasing the luminal diameter of the second elongate tubular member.

In an alternative embodiment, the elongate tubular or cylindrical balloon is toroidal in shape so that it forms a lumen from its proximal opening to its distal opening. The expandable lumen cannula is formed by inserting the second elongate tubular member through the lumen of the elongate balloon. In this embodiment, the connections previously described can be between the outer wall of the second elongate tubular member and the lumen of the elongate balloon. The outer wall of the elongate tubular member can also be sealed in a fluid-tight manner to the lumen of the elongate balloon, which can be one continuous seal along the entire length of the lumen of the elongate balloon. The elongate balloon can further comprise an inflation port for inflating the balloon.

The present invention provides an expandable lumen cannula which assists in minimally invasive aortic cannulation. The expandable lumen cannula is inserted through a port access, advancing the distal end into the ascending aorta. Fluid is introduced into the space formed between the inner wall of the cylindrical balloon and the outer wall of the flexible region of the cannula. The introduction of the fluid causes the cylindrical balloon and the flexible region of the cannula to expand, thereby causing the luminal diameter of the flexible region of the cannula to increase. Oxgenated blood then can be infused through the lumen of the cannula into the aorta. In alternative methods, the expanded lumen of the cannula can be used to insert medical devices for the performance of surgical procedures within the aorta, carotid arteries, or any other internal body structure accessible by cannulation.

In alternative methods, an expandable lumen cannula further comprises a balloon occluder at its distal end in fluid communication with an inflation lumen and an inflation port. The expandable lumen cannula is inserted through a port access, advancing the distal end into the ascending aorta. The balloon occluder is inflated to occlude the ascending aorta, followed by inflation of the cylindrical balloon, thereby increasing the diameter of the cannula lumen. Oxygenated blood then can be infused through the lumen of the cannula into the aorta distal to the balloon occluder. In alternative methods, the expanded lumen of the cannula can be used to insert medical devices for the performance of surgical procedures within the aorta, carotid arteries, or any other internal body structure accessible by cannulation.

It will be understood that there are many advantages to using an inflatable cannula as disclosed herein. For example, the inflatable cannula of the invention can be used (1) to provide easy introduction of the cannula through a small port, (2) to provide an expanding tube that serves to gently move nearby organs and tissues out of the path during surgery, (3) to provide a conduit or port to apply other medical therapies, e.g., surgical instruments, dilatation catheters, atherectomy devices, filters, aspirators, pressure monitors, etc., (4) to provide an inflatable lumen which can accommodate large flow of fluid, e.g., oxygenated blood, into the aorta or other internal body structure, (5) to provide better contact and therefore stabilization between the cannula and the arterial wall by having cannula threads at the point of contact with the vessel wall, (6) to provide interruption of arterial flow through inflating the balloon occluder, thus minimizing damage to the arterial wall and reducing the risk of emboli dislodgment as compared to traditional clamping.

DETAILED DESCRIPTION OF THE PREFERRED EMBODIMENTS

The devices and methods of the invention facilitate cannulation of the aorta through a minimally invasive port access incision during minimally invasive CABG surgery. In addition, the invention facilitates thorascopic and/or endovascular delivery of cardioplegic fluid to the myocardium so as to paralyze the heart. The invention also provides devices and methods to accommodate large flow of oxygenated blood during cardiopulmonary bypass without need for peripheral access. Once the patient is on cardiopulmonary bypass, a variety of thorascopic, endovascular, or open surgical procedures may be performed, including coronary artery bypass grafting (CABG), heart valve repair, and replacement, septal defect repair, removal of atrial myxoma, patent foramen ovale closure, treatment of aneurysms, myocardial drilling, electrophysiological mapping and ablation, and correction of congenital defects.

Figures 1, 2:
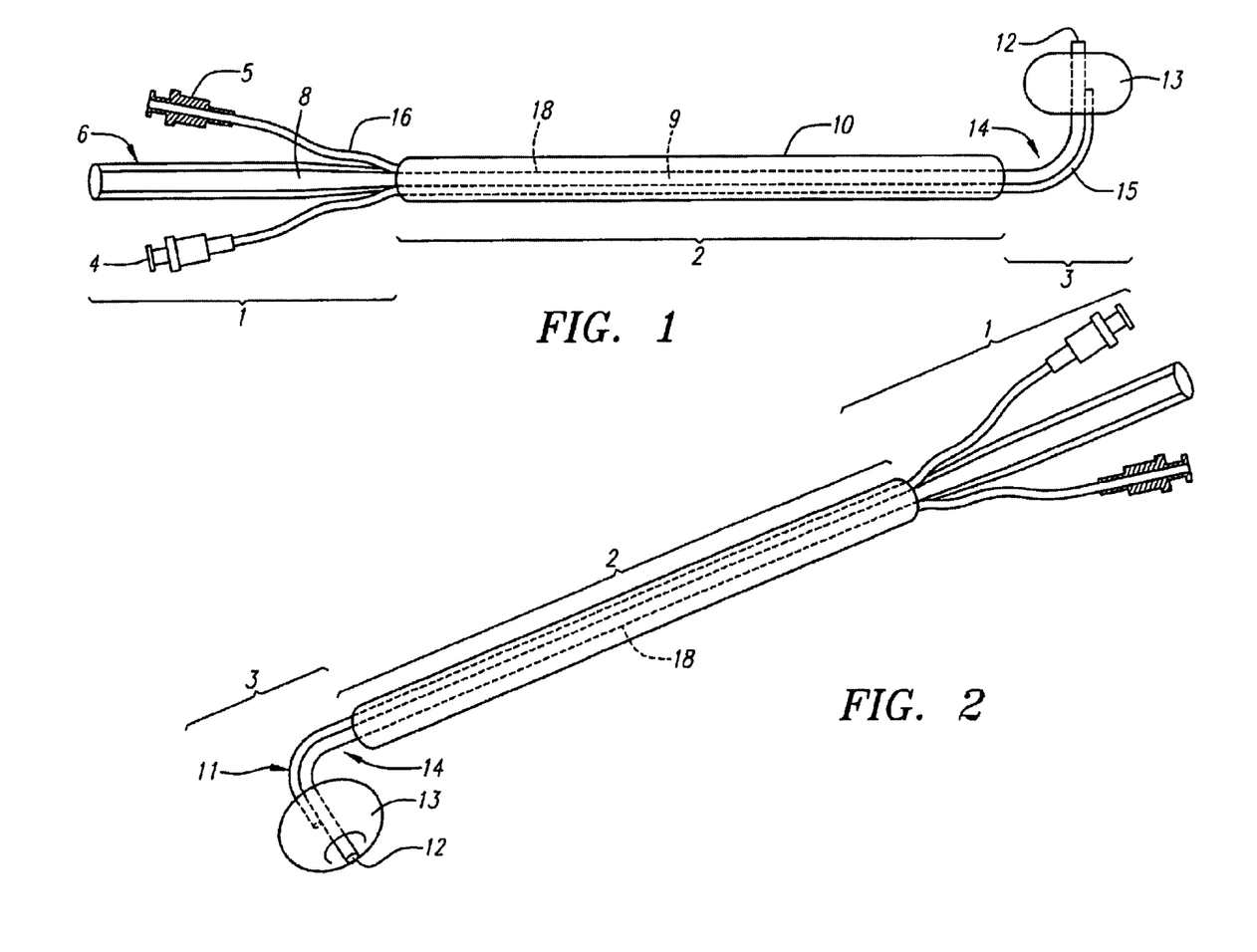
FIG. 1 depicts an embodiment of an inflatable cannula.
FIG. 2 is an oblique view of the inflatable cannula.

FIG. 1 depicts an embodiment of an inflatable cannula. The cannula has a proximal region 1, intermediate region 2, and a distal region 3. The proximal region 1 has tube 6 comprising a fixed lumen 8. Inflation ports 4 and 5 arise from the junction of the proximal and intermediate region. Inflation port 4 is responsible for inflating the balloon occluder. Inflation port 5 is responsible for inflating the cylindrical balloon. Intermediate region 2 comprises the inflatable cylindrical balloon 10, expandable cannula 18 with lumen 9, and balloon occluder lumen 15.

FIG. 2 depicts an oblique view of the inflatable cannula. Distal region 3 includes an angulated lumen port 12 for delivery of blood products and other instruments, and the balloon occluder 13 with its communicating inflation lumen 15. Helical threads 14 are located on the distal cannula close to the junction of the intermediate region.

Figures 3, 4:
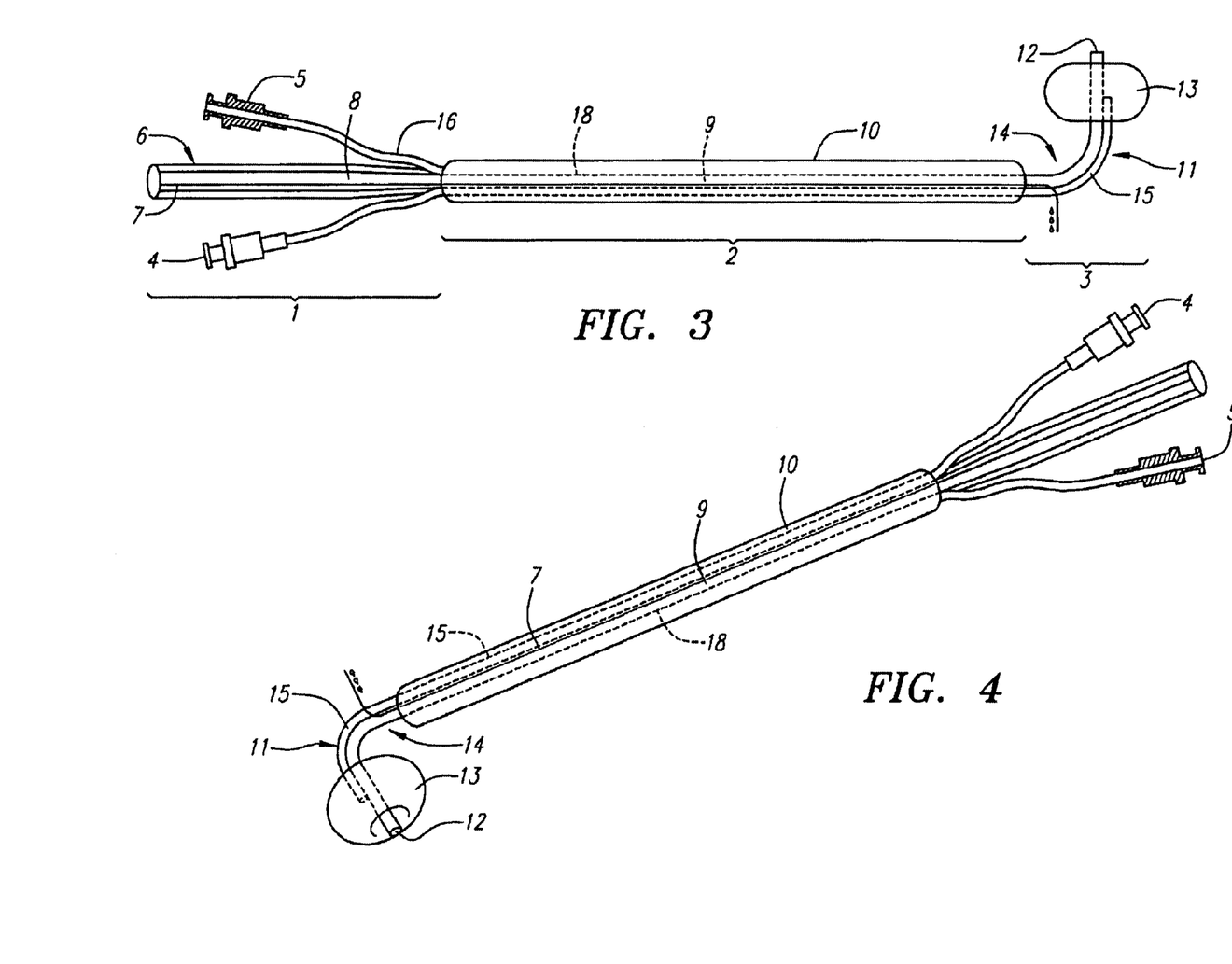
FIG. 3 depicts an embodiment of an inflatable cannula having a cardioplegia lumen and port.
FIG. 4 is an oblique view of the inflatable cannula having the cardioplegia lumen and port.

FIG. 3 depicts an embodiment of an inflatable cannula having an optional cardioplegia lumen 7 and cardioplegia ports 11 at the distal end.

FIG. 4 depicts an oblique view of an inflatable cannula having cardioplegia lumen 7 and cardioplegia port 11 at the distal end thereof.

Figure 5:
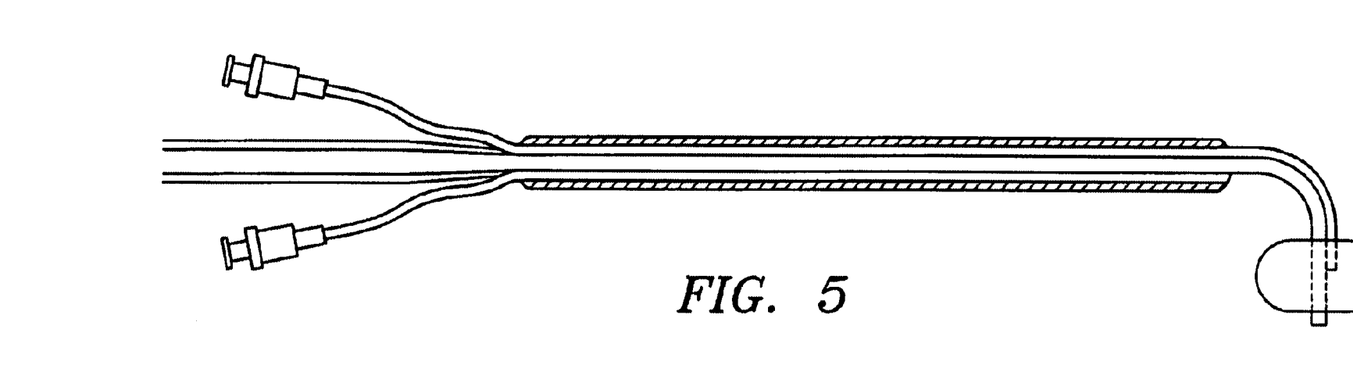
FIG. 5 depicts the deflated state of the inflatable cannula.

FIG. 5 depicts an inflatable cannula in the deflated condition. As can be seen, deflation of cylindrical balloon 10 minimizes the cross-sectional diameter of the inflatable cannula for access to a minimal incision port.

Figure 6:
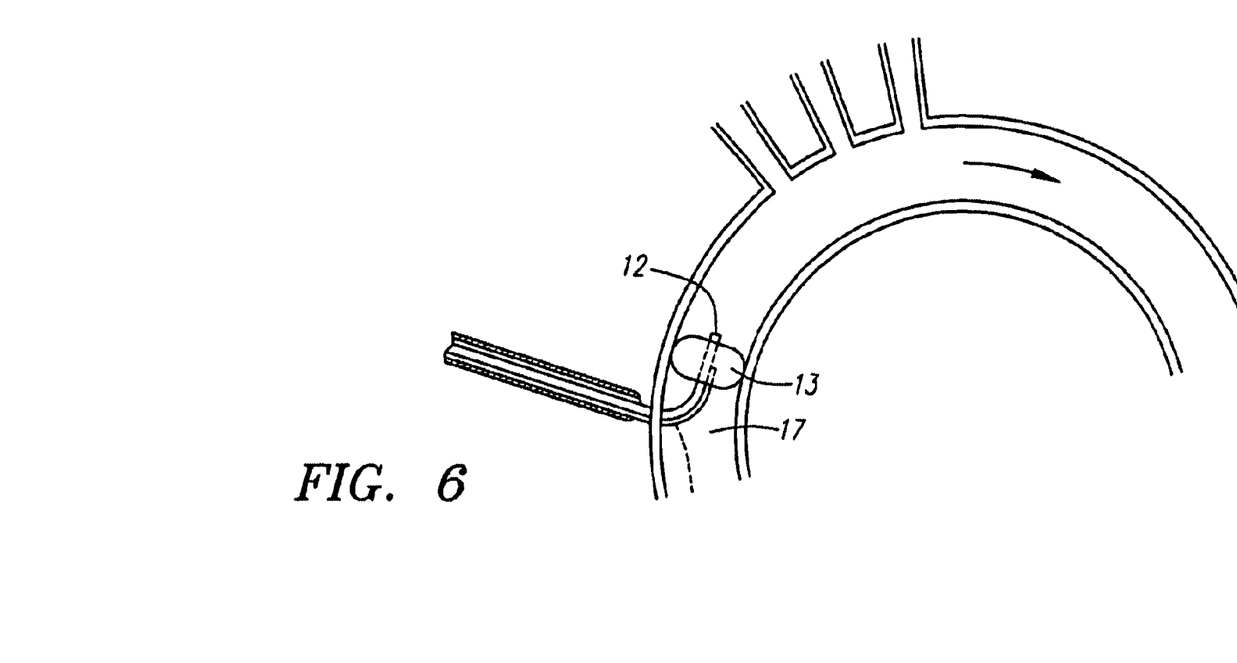
FIG. 6 depicts the position of the inflatable cannula deployed within the ascending aorta during cardiac surgery.

FIG. 6 shows an inflatable cannula deployed within the ascending aorta 17 during cardiac surgery. Balloon occluder 13 provides a gentle seal against the aortic wall. Blood products or instruments can be delivered through the end port 12 of the cannula downstream to the aorta, while cardioplegia can be delivered through cardioplegia port 11 upstream to the heart.

Figure 7:
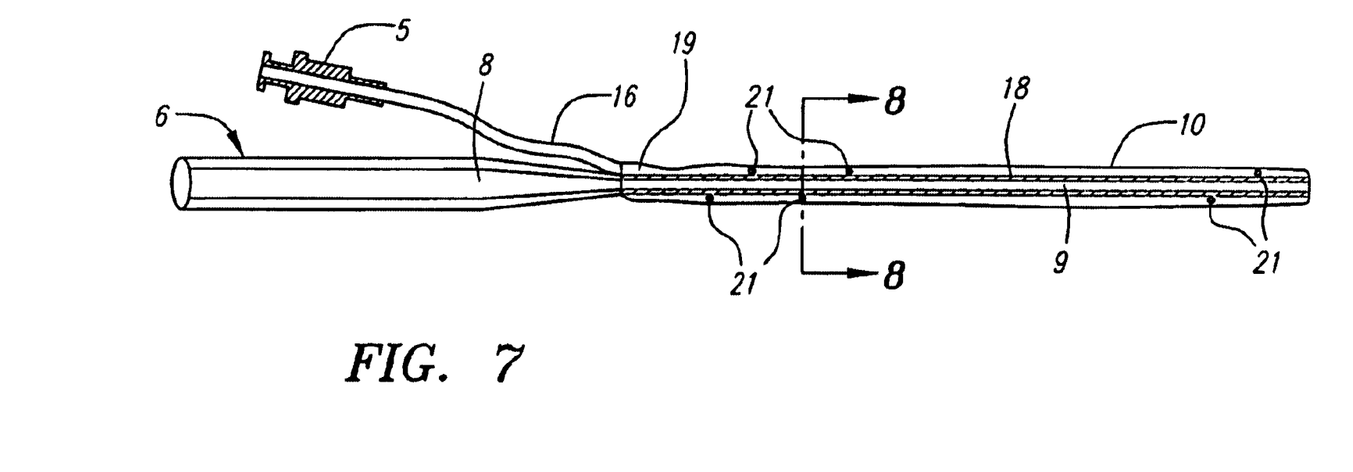
FIG. 7 depicts an embodiment of an inflatable cannula in a deflated state.

FIG. 7 shows an inflatable cannula in the deflated condition. As can be seen, the inflatable cannula comprises a proximal region 1, and a distal region 2. The proximal region includes a tube 6 having a fixed lumen 8 and an inflation port 5 in fluid communication with an inflation lumen 16. The distal region 2 includes a expandable cannula 18 having a lumen 9, an elongate cylindrical balloon 10, and space 19 formed between the inner wall of the elongate cylindrical balloon 10 and the outer wall of the expandable cannula 18.

The inner wall of the elongate cylindrical balloon 10 is connected at various points to the out wall of the expandable cannula 18. These connections 21 can either be at random points or can be formed in a predetermined pattern. Thus, when the elongate cylindrical balloon 10 inflates, it exerts an outward expanding force on the expandable cannula 18, so that the expandable cannula also expands and increases in luminal diameter.

The expandable cannula 18 can be made from such materials as Polyethylene Tetraflouride (Teflon®), urethane, nylon, or any other semi-rigid and expandable material or suitable medical grade plastic. In a preferred embodiment, the fleixble cannula 18 is non-elastic.

The elongate cylindrical balloon 10 is made of an elastomeric material and is also expandable. It can be made from such materials as silicon, latex, polyurethane, polyimide or any other expandable and elastomeric material. Furthermore, the elongate cylindrical balloon 10 is more flexible and expandable than the expandable cannula 18.

The proximal end of the expandable cannula 18 can be connected to or integrally formed with the distal end of the tube 6 so that lumen 8 of the tube 6 and lumen 9 of the expandable cannula 18 are in fluid communication. The elongate balloon 10 has openings at its proximal and distal ends. The proximal opening of the elongate cylindrical balloon 10 is sealed around the circumference of the proximal end of the expandable cannula 18 in a fluid-tight manner. Inflation lumen 16 is in fluid communication with the space 19 either through an opening on the wall of the elongate cylindrical balloon 10, or through an opening in the proximal end of the elongate cylindrical balloon 10, such as an opening in the seal formed between the proximal opening of the balloon 10 and the proximal end of the expandable cannula 18. In the latter case, the proximal end of the elongate cylindrical balloon 10 is sealed in a fluid tight manner around the combination of the inflation lumen 16 and the expandable cannula 18. The distal opening of the elongate cylindrical balloon 10 is sealed around the circumference of the distal end of the expandable cannula 18 in a fluid-tight manner.

Figure 8:
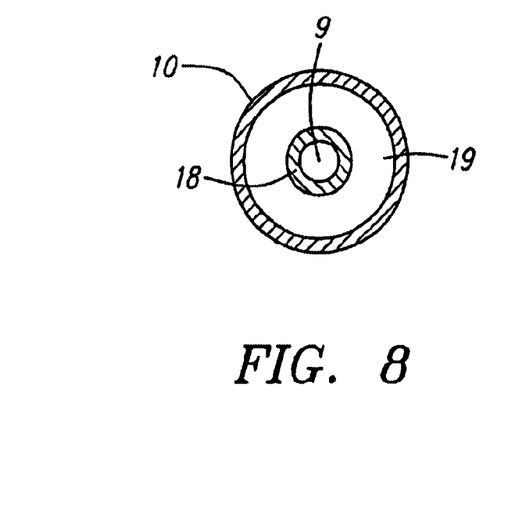
FIG. 8 is a cross-section taken through line 8—8 of FIG. 7.

FIG. 8 shows a cross section of the distal region 2 of the inflatable cannula when the cannula is in a deflated condition. It is apparent that the elongate cylindrical balloon 10 is wrapped closely around the expandable cannula 18, thus compressing the expandable cannula 10. In this state, the luminal diameter of the expandable cannula 18 is at its minimum value. The diameter of the combination of the expandable cannula 18 and elongate cylindrical balloon 10 is also at its minimum value. The outer wall of the expandable cannula 18 and the inner wall of the elongate balloon 10 are joined at connections 21, which may be randomly spaced or made in predetermined patterns.

In an alternative embodiment, an elongate cylindrical sleeve (not shown) with little or no expansion properties can be used to compress the combination of the expandable cannula 18 and the elongate cylindrical balloon 10. The sleeve can have a diameter that is smaller than the diameter of the expandable cannula 18 when the expandable cannula 18 is in its expanded state. The sleeve can be the length of the expandable cannula 18 or the elongate cylindrical balloon 10. The sleeve is also removable so that when it is removed the elongate cylindrical balloon 10 can be inflated thus expanding the luminal diameter of the expandable cannula 18, as well as the luminal diameter of the combination of the expandable cannula 18 and the elongate cylindrical balloon 10.

In a method of using such an inflatable cannula, an incision is made in the patient, for example, on the aortic wall of the patient. The distal end of the inflatable cannula is then inserted through the incision into the aorta. The sleeve is then removed by such methods as pulling it proximally until it no longer covers the elongate cylindrical balloon 10. Alternatively it can be cut off or it can be torn along a perforation along its length. Once the sleeve is removed, the elongate cylindrical balloon 10 can be inflated, thus expanding the luminal diameter of the expandable cannula 18 as well as the luminal diameter of the combination of the expandable cannula 18 and the elongate cylindrical balloon 10.

Figure 9:
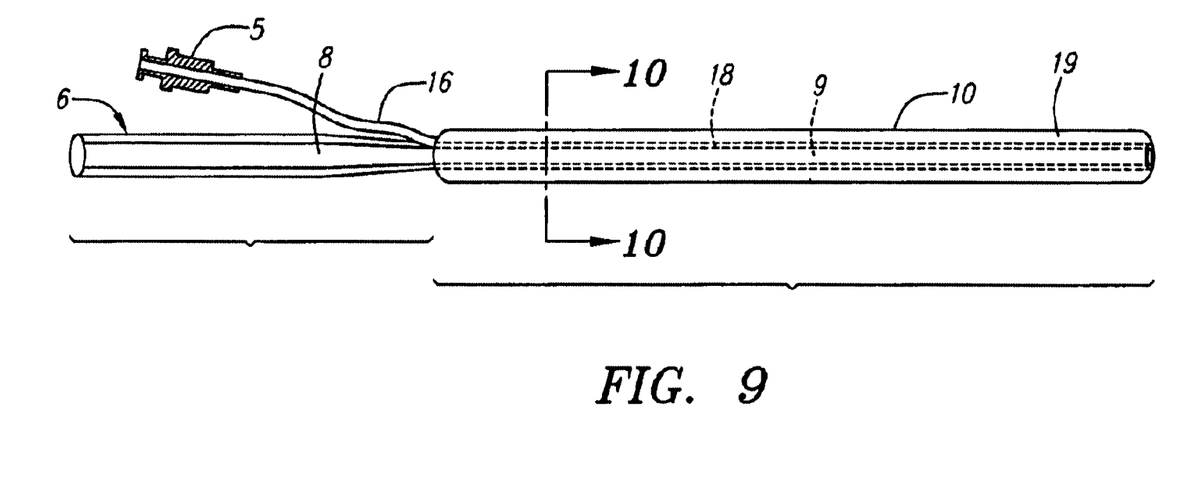
FIG. 9 depicts the inflatable cannula of FIG. 7 in an inflated state.

FIG. 9 shows the inflatable cannula of FIGS. 7 and 8 in an inflated condition. It is apparent that fluid has been introduced through inflation lumen 16 into space 19 thus expanding the elongate cylindrical balloon 10. As can be seen, inflation also causes the luminal diameter of the expandable cannula 18 to increase. Consequently, the diameter of the combination of the expandable cannula 18 and the elongate cylindrical balloon 10 also increases. This increase in the diameter of the combination allows for displacement of tissue when the distal region is inserted through an incision.

Figure 10:
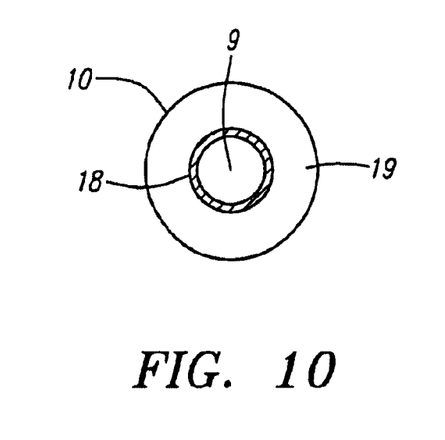
FIG. 10 is a cross-section taken through line 10—10 of FIG. 9.

FIG. 10 shows a cross-section of the distal region 2 when the elongate cylindrical balloon is inflated. As can be seen, the luminal diameter of the expandable cannula 18 is increased, allowing for passage of blood products and medical instruments. Furthermore, the luminal diameter of the combination of the expandable cannula 18 and the elongate cylindrical balloon 10 is also increased, allowing for displacement of tissue.

Figure 11:
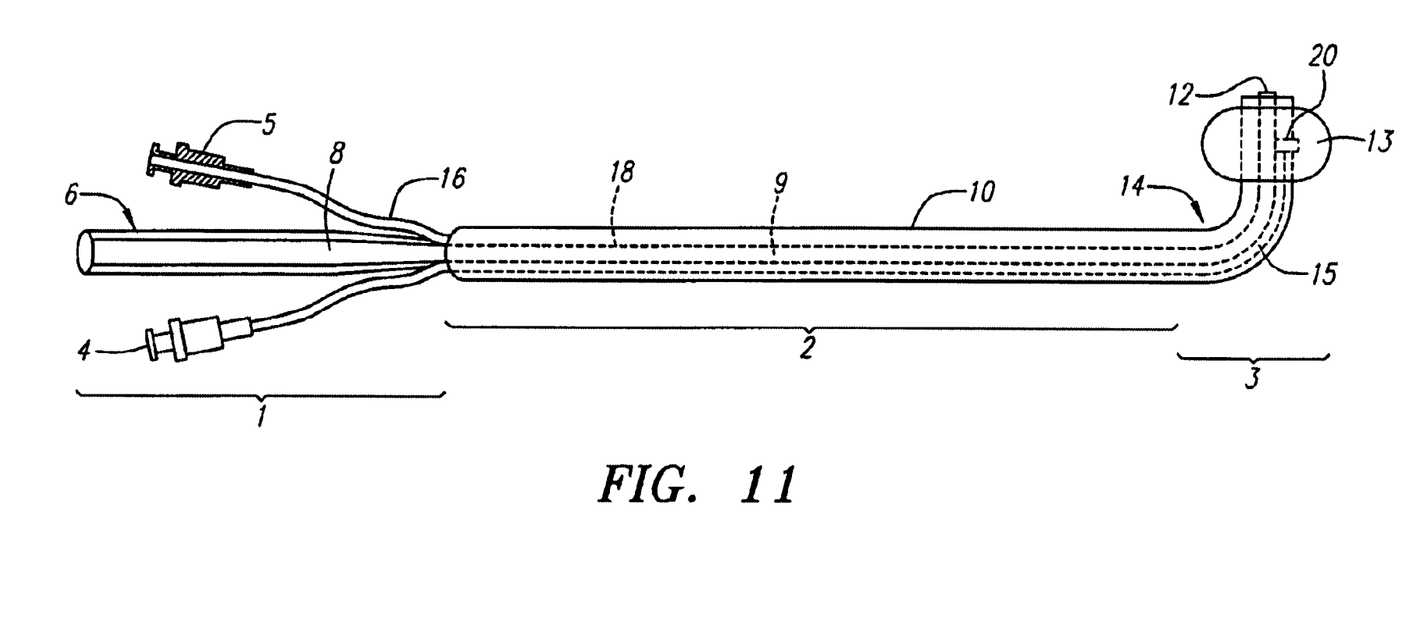
FIG. 11 depicts another embodiment of an inflatable cannula.

FIG. 11 shows an inflatable cannula having an elongate cylindrical balloon 10 disposed about a flexible region of the cannula 18, as well as a balloon occluder inflation lumen 15, wherein the elongate cylindrical balloon 10 is shown in its inflated condition. The elongate cylindrical balloon 10 covers almost the entire length of the expandable cannula 18 and balloon occluder inflation lumen 15, including the curved distal region 3. The balloon occluder 13 is circumferentially disposed around the elongate cylindrical balloon 10. The elongate cylindrical balloon 10 has an opening 20 on its distal end through which the balloon occluder inflation lumen 15 is fitted. The opening 20 can be sealed in a fluid-tight manner around the outer wall of the balloon occluder inflation lumen 15 so that when fluid is introduced into the elongate cylindrical balloon 10, it does not leak through the opening and into the balloon occluder 13.

Meanwhile, the proximal and distal openings of the balloon occluder 13 can be sealed in a fluid-tight manner around the outer wall of the elongate cylindrical balloon 10.

The elongate cylindrical balloon 10 can be made of different materials along its length. For example, along region 2, the elongate cylindrical balloon 10 can be made of an elostomeric material such as latex, while the section surrounded by the balloon occluder 13 can be made of a less elostomeric and more rigid material such as polyethylene tetraflouride, urethane, nylon, or any medical grade semi-rigid and expandable plastic.

Figures 12, 13, 14A, 14B:
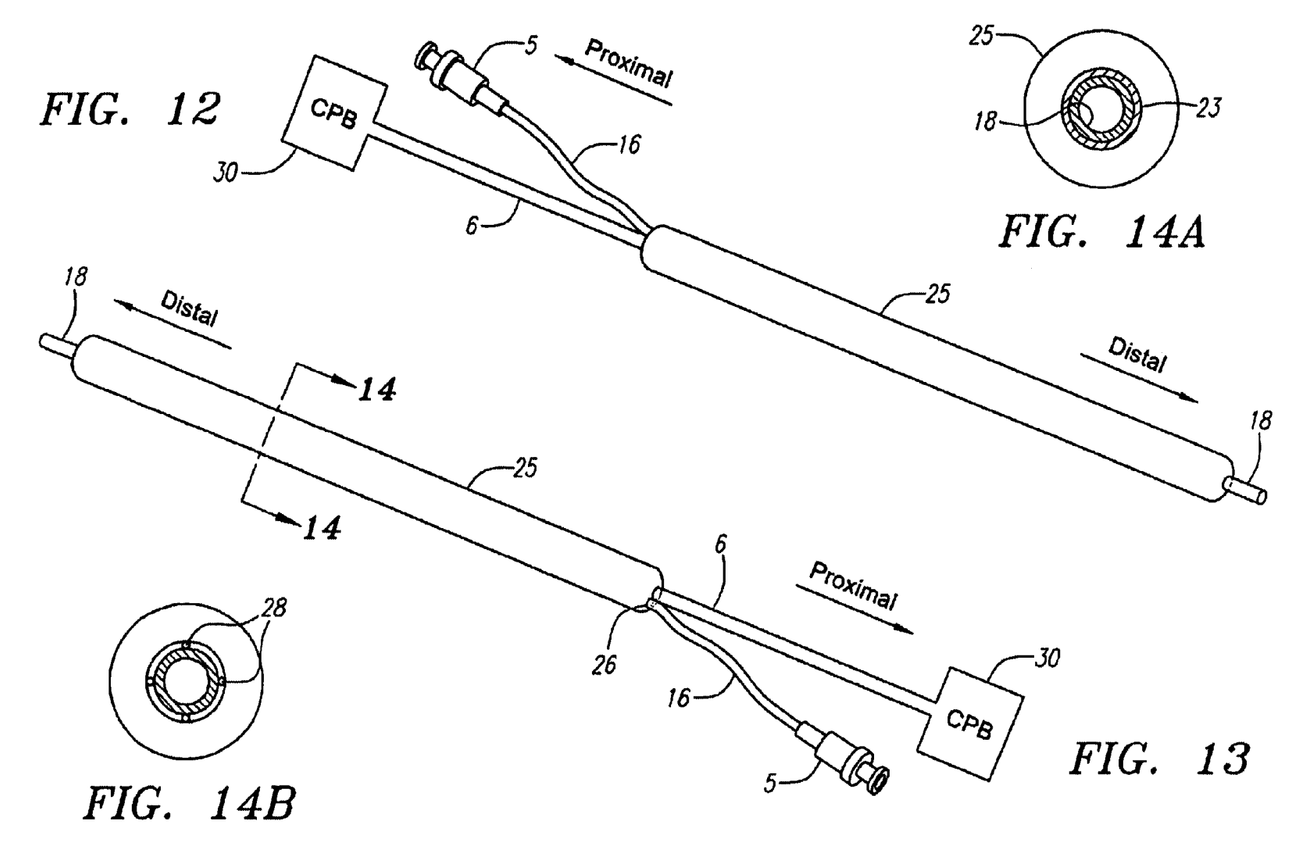
FIG. 12 is a perspective view of an embodiment of an inflatable cannula from the distal end of the cannula.
FIG. 13 is a perspective view of the inflatable cannula depicted in FIG. 12 from the proximal end of the cannula.
FIG. 14A is a cross-section taken along lines 14—14 of FIG. 13.
FIG. 14B is a cross-section taken along lines 14—14 of FIG. 13, showing an alternative embodiment of the inflatable cannula depicted in FIG. 13.

In yet another embodiment as shown in FIGS. 12 through 14, the expandable cannula 18 is surrounded by an elongate cylindrical balloon 25, which is toroidal in shape. In FIGS. 12 through 14, the elongate cylindrical balloon 25 and expandable cannula 18 are shown in an inflated state. In their original state, the balloon 25 is not inflated and is used to compress the expandable cannula 18. Alternatively, as described above, a removable elongate cylindrical sleeve can be used to compress the combination of the balloon 25 and the expandable cannula 18.

The elongate cylindrical balloon 25 forms a lumen running along the length of the balloon 25 with openings at its proximal and distal ends. This embodiment of the inflatable cannula can be made by inserting the expandable cannula 18 through the lumen of the balloon 25, so that the distal end of the expandable cannula 18 is protruding through the distal opening of the lumen of the balloon 25, and the proximal end of the expandable cannula 18 extends proximally from the proximal opening of the lumen of the balloon 25. The outer wall of the expandable cannula 18 can be sealed along its length to the lumen of the balloon 25. FIG. 14A shows a cross-section of the expandable lumen cannula with a complete seal 23 formed between the outer wall of the expandable cannula 18 and the lumen of the balloon 25. The outer wall of the expandable cannula 18 can be glued or otherwise connected in any manner at predetermined points to the lumen of the balloon 25. FIG. 14B shows the connections 28 formed between the outer wall of the expandable cannula 18 and the lumen of the balloon 25. These can be randomly formed along the length of the lumen of the balloon 25. Alternatively, the lumen of the balloon 25 can be connected to the outer wall of the expandable cannula 18 in a known pattern, such as the formation of a series of connecting rings (not shown) at predetermined intervals along the length of the lumen of the balloon 25. Inflation of the balloon 25 causes it to expand, exerting an outward expanding force, thus causing the expandable cannula 18 to expand and to increase in diameter.

FIG. 13 shows the opening 26 to which the inflation lumen 16 is sealed in a fluid-tight manner. The elongate cylindrical balloon 25 can be inflated by introducing fluid through the opening 26, thus expanding the luminal diameter of the balloon 25 and the luminal diameter of the expandable cannula 18, as well as expanding the luminal diameter of the combination of the expandable cannula 18 and the balloon 25.

The length of region 2 will generally be between 10–20 centimeters, more preferably between 12 and 15 centimeters, with a tube O. D. between 0.3 and 2.0 centimeters, more preferably 0.4–1.0 centimeters, more preferably 0.5–0.7 centimeters, more preferably approximately 0.6 centimeters. In certain embodiments, the cannula will have a circular cross-section. In other embodiments, the cannula will have an oval cross-sectional shape to more easily fit through the ribs, or it may have any other suitable shape. The inner diameter of lumen 9, when expanded, will generally be between 0.2 and 2.0 centimeters, more preferably 0.3–1.0 centimeters, more preferably 0.4–0.8 centimeters. The length of proximal region 1 will generally be between 2 and 10 centimeters, more preferably about 5 centimeters. The tube diameter and proximal region 1 is generally 0.3–1.0 centimeters, while the diameter of lumen 8 in proximal region 1 is about 0.2–0.8 centimeters. In curved distal region 3, when expanded, the balloon occluder will generally have a diameter between 1 centimeter and 2.5 centimeters, more preferably between 1.5 and 2.0 centimeters. The foregoing ranges are set forth solely for the purpose of illustrating typical device dimensions. The actual dimensions of a device constructed according to the principles of the present invention may obviously vary outside of the listed ranges without departing from those basic principles.

It is contemplated that the inflatable cannula disclosed herein will be used to perform any of the procedures including coronary artery bypass surgery, valve repair, septal defect repair, and thoracic aortic aneurysm (TAA) repair. A typical coronary artery bypass surgery (CABG) using minimally invasive procedures and the cannula disclosed herein generally begins with incubation of the patient after induction of anesthesia as explained in Reichenspurner et al., *Annals of Thoracic Surgery* 65:413–419 (1998), incorporated herein by reference. The right internal jugular vein is punctured using a 9 French introduction system for later insertion of the endopulmonary vent catheter. The patient is placed in a supine position. A small (6–8 centimeter; medium 7 centimeter) incision is made parasternally between the ribs, usually on top of the fourth rib. During dissection and removal of the cartilagenous part of the fourth rib, left internal mammary artery (LIMA) is dissected free. Thorascopic preparation of the LIMA is also accomplished through three small lateral chest ports. When complete visualization of the LIMA is not possible through the mini-thoracotomy, the inflatable cannula can then assist in the above endoscopic dissection of LIMA by its ability to accommodate instruments through its expandable lumen. As the LIMA is being prepared, a 21 French venous cannula is inserted into the femoral vein and positioned into the right atrium using transesophageal echocardiography (TEE).

Before the initiation of cardiopulmonary bypass (CPB), the inflatable cannula, in its deflated state, can be inserted through a small port and guided into the ascending aorta using thoroscopy and TEE. A Swan-Ganz catheter for pressure monitoring is often inserted through the right internal jugular vein. As shown in FIG. 7, the elongate cylindrical balloon 10 in its deflated state will exert a compressive force against the expandable cannula 18, allowing for insertion of the inflatable cannula through a small incision. Alternatively, the elongate cylindrical balloon 10 and expandable cannula 18 can be covered with a elongate cylindrical sleeve (not shown), which applies a compressive force on both the balloon 10 and the cannula 18 to reduce the luminal diameter of the cannula in its deflated state. Once the inflatable cannula has been inserted through the port, the sleeve can be removed by pulling it proximally or cutting or tearing it along a longitudinal perforation.

After LIMA is prepared for anastomosis, CPB is initiated and the balloon occluder 13 is inflated with approximately 15–30 cc of diluted radiological contrast medium using fluoroscopy and TEE. The balloon occluder 13 is generally placed about 2 centimeters above the aortic valve with careful monitoring of the right radial artery pressure to avoid occlusion of the brachiocephalic trunk by the endo-aortic balloon. The cylindrical balloon 10 is then inflated by introducing fluid into the space formed between the outer wall of the expandable cannula 18 and the inner wall of the cylindrical balloon 10. The introduction of fluid causes the balloon 10 to expand, thus exerting an outward expanding force on the outer wall of the expandable cannula 18 through connections 21. Therefore, inflation causes the luminal diameter of the expandable cannula 18 to increase, thereby allowing for free passage of oxygenated blood for CPB. Inflation also causes the cylindrical balloon 10 to expand thereby displacing adjacent tissues and organs.

After exact positioning of the balloon occluder 13, cardioplegia can be administered through the optional cardioplegia port at the distal region of the inflatable cannula. Once cardioplegic arrest is achieved, an end-to-end anastomosis is performed of the LIMA to the left anterior descending coronary artery (LAD). On completion of anastomosis, the balloon occluder and the cylindrical balloon are deflated, and the cannula is removed. The heart is reperfused and the patient is weaned from CPB. After hemostasis is obtained, the femoral cannula is removed, one chest tube is inserted, and the thoracic and femoral incisions are closed.

Similar steps as described above for minimally invasive CABG can be employed in aortic or mitral valvular replacement. The inflatable cannula is inserted through a small chest port to reach the ascending aorta. After the balloon occluder 13 is inflated, the cylindrical balloon 10 is inflated to expand the luminal diameter of the expandable cannula 18 to accommodate large flow of oxygenated blood from the CPB machine. After CPB is initiated, the damaged aortic or mitral valve can be excised and a prosthetic or porcine valve can then be sutured in place. After the valve replacement is complete, the balloon occluder 13 and the cylindrical balloon 10 are deflated and removed. The patient is weaned from CPB, a chest tube is placed, and the femoral and chest incisions are closed.

Atrial septal defect (ASD) and ventricular septal defect (VSD) can also be repaired in a similar fashion using the inflatable cannula disclosed herein. Again, the inflatable cannula is inserted through a small chest port to reach the ascending aorta. The cylindrical balloon 10 is inflated following inflation of the balloon occluder 13 to provide expanded luminal diameter of the expandable cannula 18 to accommodate large flow of oxygenated blood from the CPB machine. After CPB is initiated, cardiac incision is made to expose the ASD or VSD. A mesh is sutured securely around the defect, and the incision on the heart is closed. The inflatable cannula is removed after the balloon occluder 13 and the cylindrical balloon 10 are deflated. After the patient is weaned from CPB, the chest and femoral incisions are closed.

The inflatable cannula can also assist in repair of thoracic aortic aneurysm (TAA) by providing an expanded conduit for the oxygenated blood from the CPB machine. After sternotomy, the expandable cannula can be inserted distal to the aneurysm and inflated to provide an expanded lumen. The diseased aneurysmal aorta is resected and replaced with collagen saturated Dacron™ graft. The balloons on the cannula are then deflated and the cannula is withdrawn after the patient is weaned from CPB.

In various pediatric cardiac surgeries, such as ASD, truncous arteriosis, tetralogy of Fallot, anomalous coronary artery, Ebstein's malformation of the tricuspid valve, heart/ lung transplantation and total anomalous pulmonary vein repair, CPB is commonly indicated post-operatively due to a low cardiac output state. The inflatable cannula can easily be left in place post-operatively to provide easy access to the CPB.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A method of minimally invasive aortic cannulation, comprising the steps of:

providing an expandable lumen cannula comprising an elongate tubular member having a proximal end, a distal end, and a lumen therebetween, and an elongate balloon circumferentially disposed about the elongate tubular member;

inserting the expandable lumen cannula through a port access, and advancing the distal end of the cannula into the ascending aorta; and inflating the elongate balloon, thereby increasing the luminal diameter of the cannula and widening the port access by displacing an adjacent tissue or organ.

2. The method of claim 1, further comprising the step of infusing fluid through the lumen of the elongate tubular member into the aorta.

3. The method of claim 2, wherein the fluid is oxygenated blood.

4. The method of claim 2, wherein the elongate tubular member further comprises a balloon occluder mounted on the distal end, and wherein the method further comprises the step of inflating the balloon occluder.

5. The method of claim 4, wherein the fluid is infused into the aorta distal the balloon occluder.

6. The method of claim 1, further comprising the step of performing cardiopulmonary bypass.

7. The method of claim 1, further comprising the step of performing coronary artery bypass graft.

8. The method of claim 1, further comprising the step of performing a valve replacement.

9. The method of claim 1, further comprising the step of performing thoracic aortic aneurysm repair.

10. The method of claim 1, further comprising the step of performing septal defect repair.

11. The method of claim 1, wherein an elongate sleeve is disposed circumferentially about the elongate balloon, the method further comprising the step of removing the sleeve.

12. The method of claim 1, wherein the expandable lumen cannula further comprises a cardioplegia lumen terminating in a cardioplegia port at the distal end of the cannula, and wherein the method further comprises the step of infusing cardioplegia solution into the aorta.

13. The method of claim 1, further comprising the steps of:

inserting a medical instrument through the proximal end of the elongate tubular member; and advancing the medical instrument through the lumen of the elongate tubular member and into the ascending aorta.

* * * * *